United States Patent [19]

Nevyas

[11] Patent Number: 4,589,147
[45] Date of Patent: May 20, 1986

[54] INTRAOCULAR LENS

[76] Inventor: Herbert J. Nevyas, 1120 Tower La. East, Narberth, Pa. 19072

[21] Appl. No.: 354,826

[22] Filed: Mar. 4, 1982

[51] Int. Cl.⁴ .............................. A61F 1/16; A61F 1/24
[52] U.S. Cl. .......................................................... 623/6
[58] Field of Search .......................................... 3/13, 1

[56] References Cited

U.S. PATENT DOCUMENTS

| 4,159,546 | 7/1979 | Shearing | 3/13 |
| 4,249,271 | 2/1981 | Poler | 3/13 |
| 4,298,995 | 11/1981 | Poler | 3/13 |
| 4,403,353 | 9/1983 | Tennant | 3/13 |
| 4,418,431 | 12/1983 | Feaster | 3/13 |
| 4,504,981 | 3/1985 | Walman | 3/13 |

OTHER PUBLICATIONS

Model PC-11 Posterior Chamber Intraocular Lenses, American Medical Optics (4 page advertisement) Aug. 1981.
"The Intraocular Implant Lens Development and Results", pp. 16-23, published by Williams & Wilkins Co., Baltimore, Maryland, 1975.

Primary Examiner—Ronald L. Frinks
Attorney, Agent, or Firm—Seidel, Gonda, Goldhammer & Abbott

[57] ABSTRACT

An intraocular lens which may be surgically implanted into the human eye. The lens has two sinuous support strands located at diametrically opposite sides thereof. The support strands allow the lens to be placed either in the ciliary sulcus or the capsular bag.

9 Claims, 8 Drawing Figures

INTRAOCULAR LENS

BACKGROUND OF THE INVENTION

In opthalmic surgery, following removal of the lens of the eye, an intraocular lens is implanted to take the place of the lens removed. Various type of such lenses have been proposed and are in use. Lenses designed to be placed in the posterior chamber may be implanted in either the ciliary sulcus or the capsular bag of the eye. For example, U.S. Pat. No. 4,159,546 discloses an intraocular lens supported by a plurality of flexible strands secured to the lens body. The strands permit the lens to be supported in the posterior chamber of the eye. Numerous other lens designs are shown in the *The Intraocular Implant Lens Development and Results,* published by the Williams and Wilkens Company, Baltimore, Md., 1975, pages 16-23.

Although great advances have been made over the years in intraocular lenses, the prior art designs are not without their problems. The very common "J-looped" lenses (see FIG. 1B) are made in varying sizes depending upon whether they are meant to be placed in the capsular bag or the ciliary sulcus. The J-loops are not very compressible, and therefore if a large lens is placed within the capsular bag, it is a difficult fit. On the other hand, a small lens which is meant to go into the capsular bag may "rattle about" and irritate intraocular structures and get out of position if placed in the ciliary sulcus. It is often particularly difficult for the surgeon to be sure that a lens which is meant to be placed in the capsular bag is indeed in the bag, or that one which is placed in the sulcus is indeed solely in the sulcus and not in the bag. Sometimes, one loop is placed in the bag and the second loop in the sulcus in spite of the surgeon's best efforts.

Another problem with "J-looped" lenses is their poor compressibility, which makes them difficult to insert, since once in place in the anterior chamber, they must be rotated, or "dialed" into proper position in the posterior chamber. This requires the surgeon to make two separate movements to properly place the lens.

Other prior art lenses (see FIG. 1A) have very long gently curving loops which exert gentle pressure and are easily compressible, but, because of the extreme length of the loop, the lens is much more difficult to implant. This type of lens requires intraocular manipulation to place it into position in the posterior chamber behind the iris after the lens has been placed preliminarily in the anterior chamber. Thereafter, the lens must be pushed into the eye from anterior to posterior chamber. This increased intraocular manipulation increases the risk of injury to the eye.

The present invention avoids these problems by allowing each lens support strand to be compressed radially for a considerable distance without significantly increasing the reaction force exerted outward toward the lens optic. An advantage of this design is that the lens will push outward with about the same force regardless of whether the loop is compressed mildly if it lies in the ciliary sulcus or compressed more strongly if it lies within the capsular bag.

The lens support strands of the present invention have flat or straight ends. This offers the advantage of allowing the surgeon to more readily place the lens without the need for rotating or "dialing" the lens into place.

Another advantage of this design is that the diameter of the lens becomes less critical. It is no longer necessary to use a large lens for the ciliary sulcus or a small lens for the capsular bag.

A further advantage of the present invention is that the gentle force directed radially outwardly by the loops, and the compressibility of the loops, allow the lens to be placed equally advantageously whether both strands are located in the capsular bag, in the sulcus, or one strand in each. The gentle compression is less likely to tear the zonal suspensionary ligament of the human lens.

Furthermore, the compressibility of the strands of the present invention require less intraocular manipulation to locate the lens properly within the eye. The lens of the present invention simply can be grasped by implantation forceps and be placed in one straight movement behind the iris into the ciliary sulcus or capsular bag. Thus, rotation of the lens, or "dialing", is unnecessary with the present invention. It is also easy to compress the loops in the forceps when inserting the lens, further simplifying straight-line insertion. The surgeon simply inserts the lens, places it in position and lets go.

SUMMARY OF THE INVENTION

The present invention is an intraocular lens for surgical implantation into the human eye, and comprises a lens body and two sinuous support strands each having at least one open loop portion. Each strand is attached to the lens body at diammetrically opposite locations on the periphery of the lens body. The loops are compressible radially with respect to the center of the lens for a substantial distance toward the center of the lens without substantially increasing the reaction force exerted outward toward the lens optic.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1A:
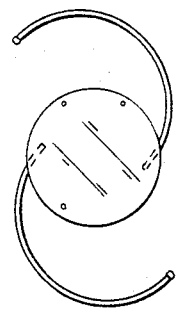
FIG. 1B shows a J-loop lens and FIG. 1A shows a lens having gently curving strands, both lenses being known in the prior art.
Figure 1B:
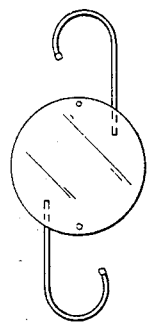
Figure 2A:
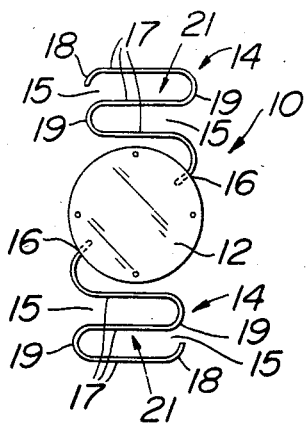
FIG. 2A is a front view of a lens in accordance with the present invention.

Referring now to the drawings, there is shown in FIG. 2A a lens in accordance with the present invention generally indicated by the numeral 10. The lens 10 comprises a lens body 12 to which are attached two support strands 14. The support strands 14, which have a sinuous, gently curving body, are attached to the lens body 12 at diammetrically opposite locations 16 on the periphery of the lens body 12. The extremities of strands 14 are provided with gently curving rounded ends 18 to minimize the possibility of damage to delicate eye tissue. The diameter of the lens body 12 defines the maximum lateral dimension of the support strands 14 in both the relaxed and compressed conditions.

The support strands 14 comprise at least two generally parallel straight legs 17 which are straight for the major portion of their length and which are joined together at one end by a generally semicircular section 19. The embodiment illustrated in the drawings employs three legs 17 and it will be appreciated that any number of legs 17 may be employed. The legs 17 define bight portions 15 at the ends opposite the semicircular section 19. Thus, the legs 17 and semicircular section 19 together form open loop portions 21.

It will be observed that, unlike support strands of prior art lenses, the ends of support strands 14 are straight or flat due to straight legs 17. When the lens is inserted into the eye, the straight end forms a chord across the circle of the iris, thereby anchoring the support strand 14 and avoiding the need for rotating or "dialing" the lens into position. This feature of the lens 10 also makes it less susceptible to rotation about a diametric axis through support strands 14.

The lens body 12 is made of a material suitable for sterilization and insertion into human tissue. Such lens materials are known in the art. The support strands 14 are made of polypropylene. Polypropylene is preferred because it has a specific gravity which is less than that of water. The amount of polypropylene in the support strands 14 is greater than the amount in other lenses because the support strands 14 have a longer total length than the support loops of prior art lenses. This makes the lens 10 of the present invention lighter than prior art lenses.

Figure 2B:
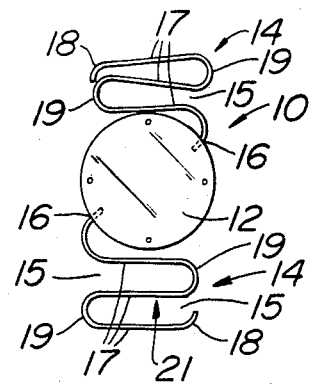
FIG. 2B shows the lens of FIG. 2A with the top strand compressed.

As shown in FIG. 2B, under compression the legs 17 move closer together. Thus, the loops formed by legs 17 and semicircular sections 19 compress radially with respect to the lens body 12. This enables the lens to be inserted straight into an incision without "dialing" to position the lens. Loops 14 compress along a radius which is angularly displaced from radii passing through diametrically opposed locations 16 where the loops 14 are attached to the lens body. The radius along which loops 14 are compressible is displaced from the closest of the radii through locations 16 by about 45°.

While loop 14 is in its compressed state, its lateral dimension does not extend beyond the diameter of the lens body 12. This feature allows the surgeon to insert the lens 10 into the eye 24 with a single straight motion.

Figure 3:
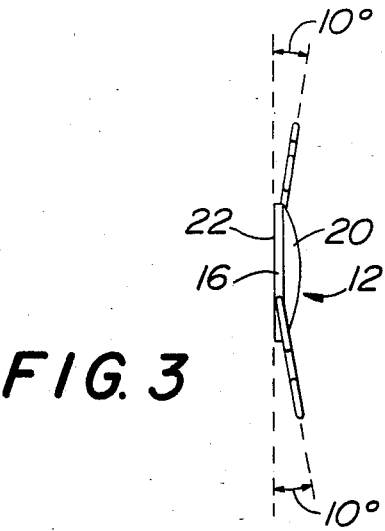
FIG. 3 is a side view of a lens in accordance with the present invention taken along the line 3—3 of FIG. 2.

As best seen in FIG. 3, lens body 12 consists of a convex portion 20 and a rim portion 22. The support strands 14 are attached to the rim portion 22 at diammetrically opposite points 16. Support strands 14 are shown arranged to form an angle of approximately 10° with the plane of the lens 12. As is known, the 10° angle of the support strands 14 to the plane of the lens provides added compressibility and keeps the lens optic well back from contact with the iris. The lens may also be constructed so that the support strands 14 are in the same plane as the lens; i.e., the angle of the support strands 14 to the plane of the lens may be zero. However, a 10° angle is preferred. Providing a 10° angle between support strands and lens plane is known in the art.

The radial length of the loops 21 should be only slightly greater than the diameter of the lens. The width of the loops 21 from side to side should not exceed the lens diameter so that the lens can be inserted straight into a minimum-sized incision.

Figure 5:
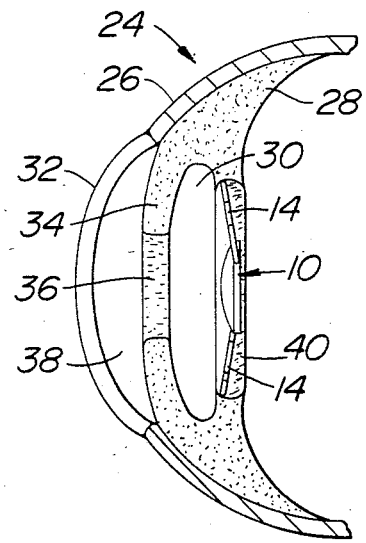
FIG. 5 is a partial cross-section of the eye showing a lens in accordance with the present invention implanted in the capsular bag.
Figure 4:
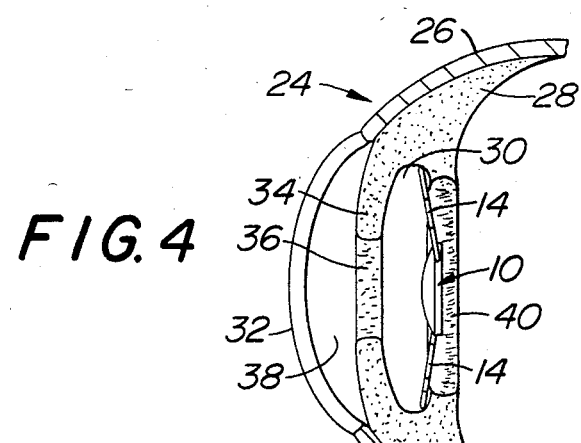
FIG. 4 is a partial cross-section of the eye showing a lens in accordance with the present invention implanted in the ciliary sulcus.
Figure 6:
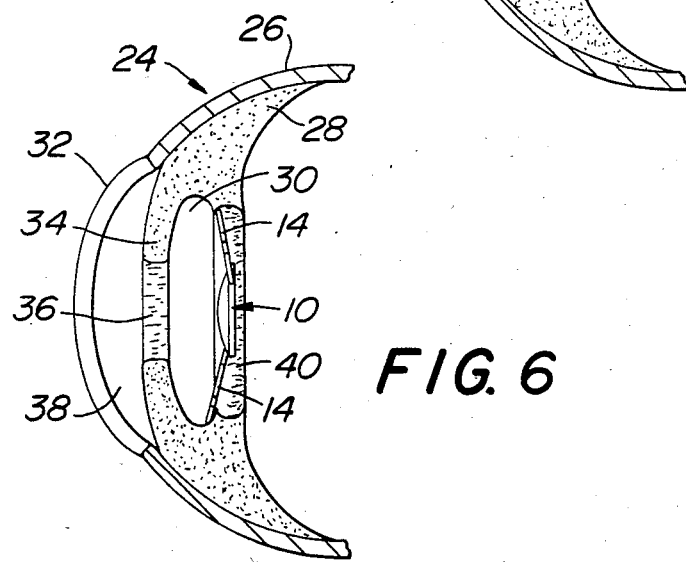
FIG. 6 is a partial cross-section of the eye showing a lens in accordance with the present invention having one support strand located in the capsular bag and the other support strand located in the ciliary sulcus.

FIGS. 4, 5 and 6 illustrate the placement of lens 10 in the eye 24. As shown in FIG. 4, the outer structure of the eye consists of the sclera 26 and the cornea 32, which together form the outer surface of the eye. The iris 34 defines the pupil or pupilary cavity 36, through which light is admitted to the interior of the eye and the retina (not shown). In FIG. 4, lens 10 is located so that support strands 14 rest in the ciliary sulcus 30, which is formed by the ciliary body 28. Since both support strands 14 are equally compressible, the lens automatically centers itself so that the optical axis of the lens coincides with the optical axis of the eye.

FIG. 5 illustrates lens 10 located in the capsular bag 40. It can be seen that, in comparison to FIG. 4, the support strands 14 are compressed greater when the lens 10 is placed in the capsular bag 40. However, because of the sinuous shape of support strands 14, the force exerted by support strands 14 against the capsular bag 40 is quite gentle. As described above, since both support strands 14 are equally compressible, lens 10 automatically aligns its optical axis with the optical axis of the eye.

FIG. 6 illustrates lens 10 located such that one support strand 14 is located in the capsular bag 40 while the other support strand 14 is located in the ciliary sulcus 30. Ordinarily, such an implantation would be disadvantageous in that the optical axis of the lens would not correspond to the optical axis of the eye because each of the support strands is compressed to a different degree, and therefore would exert a different reaction force on the lens. However, the sinuous shape of the support strands 14 in the present invention causes the strands 14 to exert virtually constant reaction forces regardless of the degree to which they are compressed. Thus, in spite of one support strand 14 being located in the capsular bag 40 and the other in the ciliary sulcus 30, both exert almost equal reaction forces and thus the lens 10 is automatically almost centered so that the optical axis of the lens 10 corresponds closely to the optical axis of the eye.

It is believed that only 0.5 mm to 1.0 mm decentration results even if one strand is in the capsular bag and the other is in the sulcus.

It will be appreciated that the invention provides an intraocular lens which is gentle on eye tissue, easily compressible and quite stable in position. The lens also includes more polypropylene than other lenses which makes its density very close to that of the aqueous material in the eye. The lens, moreover, centers well and does not have to be rotated into place.

The present invention may be embodied in other specific forms without departing from the spirit or essential attributes thereof and, accordingly, reference should be made to the appended claims, rather than to the foregoing specification, as indicating the scope of the invention.

I claim:

1. An intraocular lens for surgical implantation into posterior chamber of the human eye, comprising a lens and two sinuous support strands each having at least one open loop portion, said strands being directly attached to the lens at diametrically opposite locations on the periphery thereof, the radial length of the loops being approximately equal to the diameter of the lens and the width of the loops from side to side being not greater than the diameter of the lens, the loops being linearly compressible along a radius of the lens for a substantial distance toward the center of the lens without substantially increasing the reaction force exerted outward toward the lens optic whereby the lens will automatically align itself with the axis of the lens being substantially coaxial with the axis of the eye regardless of whether the strands are placed in the ciliary sulcus or capsular bag or one strand in each, each of said loops having generally parallel legs which are perpendicular to the longitudinal axis of the lens and which move closer together as the loops are compressed.

2. An intraocular lens as in claim 1, wherein each support strand has more than two parallel legs.

3. An intraocular lens in accordance with claim 1 wherein each loop has at least three such generally parallel legs.

4. An intraocular lens in accordance with claim 1 wherein said loops are compressible along a radius which is angularly displaced from radii passing through said diametrically opposite locations.

5. An intraocular lens in accordance with claim 4 wherein said radius is displaced from the closest of said radii by approximately 45°.

6. An intraocular lens according to claim 1 wherein the width of the loops from side to side in both the relaxed and compressed states is not greater than the diameter of the lens body.

7. An intraocular lens in accordance with claim 1 wherein the legs of each loop are generally straight and form a chord across the circle of the iris when the lens is inserted into the eye.

8. An intraocular lens for surgical implantation into the human eye, comprising a lens and two sinuous support strands each having at least one open loop portion, said strands being directly attached to the lens at diametrically opposite locations on the periphery thereof, the loops being linearly compressible along a radius of the lens which is angularly displaced by approximately 45° from radii passing through said diametrically opposite locations for a substantial distance toward the center of the lens without substantially increasing the reaction force exerted outward toward the lens optic, each of said loops having at least three generally parallel straight legs which move closer together as the loops are compressed such that the end of each loop forms a chord across the circle of the iris when the lens is inserted into the eye, the radial length of the loops being approximately equal to the diameter of the lens and the width of the loops from side to side in both the relaxed and compressed states being not greater than the diameter of the lens.

9. An intraocular lens for surgical implantation into the human eye, comprising a lens body and two sinuous support strands each having at least one open loop portion, the strands being directly attached to the lens body at diametrically opposite locations on the periphery thereof, the loops being linearly compressible radially with respect to the center along a radius of the lens for a substantial distance towards the center of the lens without substantially increasing the reaction force exerted outward towards the lens optic, each said loop having at least three generally parallel legs which move closer together as the loops are compressed, the radial length of the loops being approximately equal to the diameter of the lens and the width of the loops from side to side being not greater than the diameter of the lens in both the relaxed and compressed states.

* * * * *